United States Patent [19]

Viski et al.

[11] Patent Number: 4,613,461

[45] Date of Patent: Sep. 23, 1986

[54] PROCESS FOR PREPARING ESTERS OF THIOLCARBAMIC ACIDS

[75] Inventors: Péter Viski; László Simándi; Ferenc Nagy; Gábor Besenyei, all of Budapest; György Pászthy; Gyula Pázmándi, both of Kazincbarcika; István Szita; Gyula Szilágyi, both of Miskolc; István Tóth; Ilona Szigeti née Kiss, both of Budapest, all of Hungary

[73] Assignees: MTA Kozponti Kemiai Kutato Intezet, Budapest; Borsodi Vegyi Kombinat, Kazincbarcika, both of Hungary

[21] Appl. No.: 687,608

[22] Filed: Dec. 31, 1984

[30] Foreign Application Priority Data

Dec. 29, 1983 [HU] Hungary .............................. 4509/83
Dec. 29, 1983 [HU] Hungary .............................. 4510/83
Dec. 10, 1984 [HU] Hungary .............................. 4583/84
Dec. 10, 1984 [HU] Hungary .............................. 4584/84

[51] Int. Cl.[4] .................. C07D 211/60; C07D 207/00; C07C 153/00; C07C 154/00
[52] U.S. Cl. .................................... 540/608; 548/531; 558/232; 558/239; 546/245
[58] Field of Search .................... 260/455 A, 239 BF; 548/531; 546/245; 558/232, 239

[56] References Cited

U.S. PATENT DOCUMENTS 4,071,423 1/1978 Pitt .................................. 260/455 A

OTHER PUBLICATIONS

Noller, Textbook of Organic Chemistry, 3rd Ed., W. B. Saunders Co., Philadelphia, 1966, p. 81.
Reppe, W., Ann. 601, 81–138, 1956.
Houben–Weyl, Methoden der Organischen Chemie, vol. 5/16.

*Primary Examiner*—Henry R. Jiles
*Assistant Examiner*—Robert C. Whittenbaugh

[57] ABSTRACT

The invention relates to a new process for preparing known thiolcarbamate esters of the general formula (I)

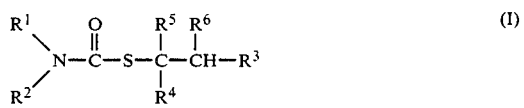

wherein $R^1$ and $R^2$ stand independently for hydrogen or a straight or branched chain alkyl group containing 1 to 6 carbon atoms or an alkenyl group containing 2 to 6 atoms, or an alkyl group containing 1 to 6 or an alkenyl group containing 2 to 6 carbon atoms and mono- or polysubstituted by halogen, oxygen, sulphur and/or nitrogen; or $R^1$ and $R^2$ together may represent an optionally substituted $\alpha,\omega$-alkylene group containing 4 to 6 carbon atoms;

$R^3$ and $R^4$ stand independently for hydrogen or an alkyl group containing 1 to 4 carbon atoms and optionally substituted by halogen or by a group containing oxygen, sulphur and/or nitrogen; and $R^5$ and $R^6$ both stand for hydrogen; or $R^5$ and $R^6$ together may represent a chemical bond.

The compounds of general formula (I) are prepared by reacting (a) thiolcarbamate salts of the general formula (II)

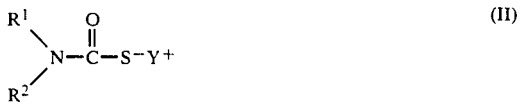

wherein the meanings of $R^1$ and $R^2$ are as defined above, and

Y stands for a primary, secondary or tertiary ammonium ion or an alkaline metal ion; or (b) amines of the general formula (III)

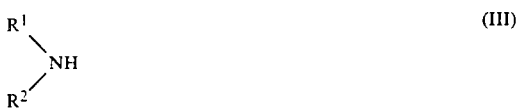

wherein the meanings of $R^1$ and $R^2$ are as defined above, together with sulphur and carbon monoxide; or (c) amine of the general formula (III) together with carbonyl sulphide with alkynes of the general formula (IV)

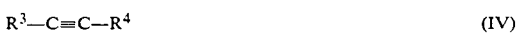

$$R^3-C\equiv C-R^4 \qquad (IV)$$

wherein the meanings of $R^3$ and $R^4$ are as defined above and, if desired, hydrogenating the obtained product of general formula (I), wherein the meanings of $R^1$, $R^2$, $R^3$ and $R^4$ are as defined above and $R^5$ together with $R^6$ forms a chemical bond, to a compound of the general formula (I), wherein both $R^5$ and $R^6$ stand for hydrogen.

18 Claims, No Drawings

PROCESS FOR PREPARING ESTERS OF THIOLCARBAMIC ACIDS

FIELD OF THE INVENTION

This invention relates to a new process for preparing known thiolcarbamate esters of the formula (I)

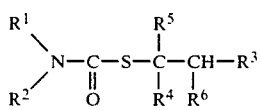

wherein
- $R^1$ and $R^2$ stand independently for hydrogen or a straight or branched chain alkyl group containing 1 to 6 carbon atoms or an alkenyl group containing 2 to 6 carbon atoms, or an alkyl group containing 1 to 6 or an alkenyl group containing 2 to 6 carbon atoms and mono- or polysubstituted by halogen, oxygen, sulphur and/or nitrogen; or
- $R^1$ and $R^2$ together may represent an optionally substituted $\alpha,\omega$-alkylene group containing 4 to 6 carbon atoms;
- $R^3$ and $R^4$ stand independently for hydrogen or an alkyl group containing 1 to 4 carbon atoms and optionally substituted by halogen or by a group containing oxygen, sulphur and/or nitrogen; and
- $R^5$ and $R^6$ both stand for hydrogen; or
- $R^5$ and $R^6$ together may represent a chemical bond.

Depending on the meanings of $R^5$ and $R^6$, the esters prepared by the process of invention are S-alkenyl thiolcarbamates (when $R^5$ and $R^6$ together represent a chemical bond) or S-alkyl thiolcarbamates (when both $R^5$ and $R^6$ stand for hydrogen).

BACKGROUND OF THE INVENTION

The S-alkanyl thiolcarbamate compounds are used in industry as plastic (synthetic) materials for the preparation of polymeric substances and as intermediates for the production of plant protecting agents; while the S-alkylthiolcarbamate compounds of the latter type are employed as active ingredients of plant protecting compositions in the agriculture.

A widely used method for preparing vinyl compounds comprises the addition of a substance containing a mobile hydrogen to acetylene. The possibilities of utilizing this method have been described by W. Reppe [Ann. 601, 81–138 (1956)] reporting on the preparation of a number of vinyl compounds; however, alkenyl esters of thiolcarbamic acids have not been disclosed.

C. G. Overberger et al. [J. Org. Chem. 27, 4331–4337 (1962)] were the first to work out a method for preparing S-(1-alkenyl)esters of monothiocarbamic acids. The principle of their method comprises the splitting off by potassium tertiary-butoxide from an S-($\beta$-chloroethyl)-monothiocarbamate prepared previously. This process, still giving good yields, did not become widely utilized in the practice because the starting materials are expensive, corrosive and toxic in character.

Practically, S-alkyl thiolcarbamates of the formula (I) are obtained by reacting a primary, secondary or tertiary ammonium salt or an alkaline metal salt of the appropriate thilcarbamic acid with an alkyl halide (Soviet patent specifications Nos. 224,511 and 186,437; DT-PS Nos. 2,513,196 and 2,844,305; Japan patent specifications Nos. 75 76026, 78 25564, 77 28832 and 77 746027; as well as U.S. Pat. Nos. 3,167,571 and 3,151,119).

According to the DT-PS Nos. 2,212,766 and 2,117,115 as well as to U.S. Pat. No. 4,066,081, phosgene is brought into reaction with alkyl mercaptans and the alkyl chlorothioformates obtained are reacted with primary or secondary amines.

S-Alkyl thiolcarbamates can also be prepared by reacting carbamoyl chloride with alkyl mercaptans (U.S. Pat. Nos. 2,983,747 and 2,913,327; as well as Spanish patent specification No. 422,149).

According to DT-PS No. 2,703,106, thiolcarbamates are obtained by treating dithiocarbamates with dimethyl sulphate and elementary iodine.

According to DT-PS No. 2,461,876 O-alkyl thiocarbamates are heated with dialkyl sulphates to give S-alkyl esters via isomerization.

According to U.S. Pat. No. 4,071,423, thiolcarbamates are obtained in an extraordinarily high yield by the radical addition of thiolcarbamate salts to olefins.

All these processes require expensive starting materials or create a severe burden upon health and environment.

OBJECT OF THE INVENTION

Thus, the objective of the invention is to provide a new advantageous process for preparing the S-alkyl and S-alkenyl thiolcarbamates, respectively, of the general formula (I).

The invention is based on the recognition that the unsaturated compounds of formula (I) can be obtained by the nucleophilic addition of salts of thiolcarbamic acids to 1-alkynes, e.g. to acetylene. It has further been recognized, that it is not essential to prepare and isolate the thiolcarbamate salts previously, but those can be obtained in situ from the reaction of the appropriate amine with carbon monoxide and sulphur or, from the appropriate amine with carbonyl sulphide, and reacted directly with the alkyne.

Further on, the invention is based on the recognition that S-alkyl thiolcarbamates of the formula (I) can be prepared by hydrogenating the S-alkenyl thiolcarbamates that in turn are easily and cheaply obtained. Hitherto, the hydrogenation of S-alkenyl thiolcarbamates to the appropriate S-alkyl derivatives has not been reported.

Thus, the present invention relates to a new process for preparing the thiolcarbamate esters of formula (I)

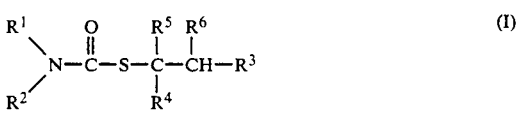

wherein the meanings of $R^1$, $R^2$, $R^3$, $R^4$, $R^5$ and $R^6$ are as defined above, which comprises reacting
(a) thiolcarbamate salts of the formula (II)

wherein the meanings of
$R^1$ and $R^2$ are as defined above, and
Y stands for a primary, secondary or tertiary ammonium ion or an alkaline metal ion; or (b) amines of the formula (III)

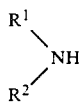

wherein the meanings of $R^1$ and $R^2$ are as defined above, together with sulphur and carbon monooxide; or (c) amines of the formula (III) together with carbonyl sulphide with alkynes of the formula (IV)

$$R^3-C\equiv C-R^4 \qquad (IV)$$

wherein the meanings of $R^3$ and $R^4$ are as defined above and, if desired, hydrogenating the obtained product of formula (I), wherein the meanings of $R^1$, $R^2$, $R^3$ and $R^4$ are as defined above and $R^5$ together with $R^6$ forms a chemical bond, to a compound of the formula (I), wherein both $R^5$ and $R^6$ stand for hydrogen.

According to the process (a) step, the thiolcarbamate salt of formula (II) is reacted with an appropriate 1-alkyne in a solution prepared with a lower aliphatic alcohol, e.g. methanol, ethanol, n-propanol, isopropanol, n-, secondary-, or tertiary-butanol, preferably with methanol, or in the presence of an inert solvent, e.g. tetrahydrofuran. This solution is reacted with the appropriated alkyne at pressures between 0.1 and 10 MPa, at temperatures between 100° and 160° C. for 2 to 10 hours.

A preferred embodiment of the process (a) step of the invention comprises preparing a possibly most concentrated solution of the thiolcarbamate salt of formula (II). A concentration of at least 30% by weight has proved to be very advantageous for achieving good yields.

The conditions for the process steps (b) and (c) of the invention are similar. The reaction temperature may be varied between wide limits, from 25° to 200° C., preferably from 80° to 160° C. It is not essential to keep the temperature at a constant level. Thus, the amine, carbon monoxide and sulphur may be reacted at about 100° C., then depending on the reactivity of the alkyne, the reaction mixture may be cooled or heated for reacting with the alkyne.

The duration of the reaction depends on the amount and reactivity of the reactants and lies between 30 minutes and 30 hours.

In general, the order of adding the reactants is not critical. It is preferred, however, to charge the required amount of the amine and sulphur into the reactor and after closing it, to rinse out with acetylene and finally, to adjust the pressure of carbon monoxide and acetylene. The reactants may be added either in batches or continuously.

The mole ratio of the amine to the sulphur may in general be varied from 5:1 to 1:5. Preferably, an excess of sulphur is used for achieving the possibly highest conversion of the amine. The suitable mole ratio of carbon monoxide to sulphur is between 1:1 and 3:1. Finally the mole ratio of the alkyne to the amine may be varied between more wide limits, from about 1:2 to about 100:1. The required amounts of lower alkynes, e.g. of acetylene result in a pressure from 0.1 to 5 Mpa in the reactor.

The reaction may be carried out in the presence of or without any solvent. Suitable solvents are lower alkanols, e.g. methanol, ethanol, propanol, isopropanol, n-, iso-, tertiary and secondary butanol, preferably methanol; aprotic polar solvents, e.g. acetonitrile, benzonitrile, dimethylformamide, dimethylsulphoxide, hexamethylphosphoramide; inert solvents, e.g. ethers such as tetrahydrofuran, dioxane, acetone; as well as teritary aliphatic amines, pyridine and its homologs; finally, aromatic hydrocarbons, chlorinated hydrocarbons, carboxylic acids and the esters of carbonic acid.

The reaction can be achieved in several cases without any solvent, i.e. in the form of a melt.

In the course of the synthesis of various S-alkenyl thiolcarbamates, a decrease in the rate of the vinylating reaction may frequently be observed toward the end of the transformation. In such cases it is advantageous to alkylate the salt not transformed in an appropriate way, in order to abbreviate the time of reaction and to accomplish a highest possible utilization of the amine. This method is particularly advisable when the S-alkenyl ester prepared will directly be transformed to the S-alkyl ester. Thus, the incompletely transformed reaction mixture is treated e.g. by diethyl sulphate or ethyl chloride for preparing the S-vinyl esters. The obtained mixture of the S-alkenyl with the S-alkyl compound is then subjected to the further processing.

In a last, facultative step of the process of invention, the obtained S-alkenyl esters of formula (I) (wherein $R^5$ and $R^6$ together represent a chemical bond) if desired, may be hydrogenated to the corresponding S-alkyl esters (wherein $R^5$ and $R^6$ are hydrogen atoms). This hydrogenation can be accomplished as a catalytic transfer hydrogenation, i.e. in the presence of a catalyst and a hydrogen donor, albeit an usual catalytic hydrogenation with gaseous hydrogen may also be used.

On employing the catalytic transfer hydrogenation [see, e.g. C. Brieget and T. I. Westrick: Catalytic Transfer Hydrogenation, Chem. Rev. 74, 567 (1974)], the unsaturated compound is hydrogenated in an appropriate solvent, in the presence of a hydrogen donor and a catalyst. An excess of the donor may also play the role of the solvent. This transfer process may be carried out in an inert, hydrogen-free, gaseous environment, however, it is more advantageous to work under a hydrogen pressure, preferably at about 0.1 to 5 MPa.

Suitable catalysts for the transfer hydrogenation are: palladium or platinum optionally on a suitable carrier, e.g. 10% palladium on activated carbon or 10% palladium on lime or 0.1% palladium on aluminum oxide; platinum black, platinum and palladium halides or oxides ($PdCl_2$, $PtO_2$) as well as Raney nickel; ruthenium, iridium or rhodium complexes, e.g. $RuCl_2(PH_3P)_3$, $IrHCl_2(Mo_2SO_4)$, $IrBr(CO)(Ph_3P)_3$ or $RhCl(Ph_3P)_3$.

It is particularly preferable to use a lower alkanol, e.g. methanol, ethanol, n- or isopropanol, n-, iso-, secondary or tertiary butanol which simultaneously play the role of both a hydrogen donor and the solvent.

The unsaturated compounds of formula (I) may also directly be hydrogenated. In this case, the relation of the substrate to the catalyst is particularly favorable. The direct hydrogenation is carried out in a pressure vessel at temperatures between 150° and 300° C., at pressures between 0.1 and 10 MPa, preferably between 1 and 5 MPa. Suitable solvents are thosementioned above for the catalytic transfer hydrogenation, but other protic solvents, e.g. glacial acetic acid may also be used. The catalysts are the commonly used hydrogenating agents, e.g. palladium, Raney nickel or platinum, optionally on a suitable carrier, e.g. aluminum oxide, silica gel, activated carbon or zeolite. An important condition is that the catalyst should not be sensitive against sulphur.

SPECIFIC EXAMPLES

The process of the invention is further illustrated by the following non-limiting Examples.

EXAMPLE 1

Process (a)

In a stainless steel autoclave of 250 ml working volume, 50 g (0.19 mole) of di(n-propyl)-ammonium N,N-di(n-propyl)-thiolcarbamate were dissolved in 100 ml of methanol. After closing the reactor, the gas phase was rinsed out with acetylene and charged with acetylene to a pressure of 1.5 MPa. Then, the autoclave was heated at 130° C. under effective stirring for several hours, cooled down and the pressure was blown off. The reaction mixture was poured into 5 volumes of water and extracted with chloroform. The organic layer was dried over anhydrous magnesium sulphate and then evaporated under reduced pressure. The residue was distilled under reduced pressure to give 23 g (61.2% yield) of S-vinyl N,N-di(n-propyl)-thiolcarbamate boiling at 105°-112° C./6 mbar.

EXAMPLE 2

Process (a)

The procedure described in Example 1 was followed, with the exception that triethylammonium N,N-diethyl-thiocarbamate was used as starting material to give 19 g (41% yield) of S-vinyl N,N-diethylthiolcarbamate.

EXAMPLE 3

Process (b)

9.6 g (0.3 mole) of sulphur, 82 ml (0.6 mole) of di(n-propyl)-amine and 100 ml of methanol were charged into a stainless steel reactor of 1000 ml working volume fitted with a stirrer and internal heating. The reactor was rinsed with acetone, then the partial pressure of acetylene and subsequently that of carbon monoxide were adjusted to 1.72 MPa. After starting the stirrer, the vessel was heated to 130° C. and kept at the same temperature for 9.5 hours, then cooled down and blown off. The reaction mixture was taken up with 100 ml of water and extracted with 3×50 ml of chloroform. The combined organic phases were dried over anhydrous magnesium sulphate, filtered, evaporated and the residue was distilled under reduced pressure to give 26.4 g (47% yield) of S-vinyl N,N-di(n-propyl)-thiolcarbamate boiling at 115° to 120° C./12-13 mbar.

EXAMPLE 4

Process (b)

9.6 g (0.3 atom) of sulphur, 82 ml (0.6 mole) of di(n-propyl)-amine and 100 ml of methanol were charged into the reactor described in Example 3. The reactor was rinsed out with carbon monoxide, then the pressure of carbon monoxide was adjusted to 1.9 MPa. After starting the stirrer, the reactor was heated to and kept at 130° C. for 90 minutes. After cooling down and blowing off, the reactor was charged with acetylene up to a pressure of 1.9 MPa, heated at 130° C. for 5.5 hours and worked up as described in Example 2 to give 23.9 g (46% yield) of S-vinyl N,N-di(n-propyl)-thiolcarbamate with the same boiling point as given for the compound obtained in Example 1.

EXAMPLE 5

Process (b)

37.3 g (1.17 atoms) of sulphur, 100 ml (0.67 mole) N-ethyl-N-cyclohexylamine and 100 ml of methanol were charged into the reactor described in Example 3. After rinsing out, the pressure of acetylene was adjusted to 1.4 MPa, while that of carbon monoxide was adjusted to 3.72 MPa. The reactor was heated up and kept at a constant temperature of 100° C. for one hour, then heated to and kept at 120° C. for 8.5 hours. Based on the analysis by gas-liquid chromatography, a conversion of 40% was achieved to give 25% yield of S-vinyl N-ethyl-N-cyclohexylthiolcarbamate boiling at 122°-124° C./2.6 mbar.

EXAMPLE 6

Catalytic transfer hydrogenation 2 g (12.5 mmoles) of S-vinyl N,N-diethylthiolcarbamate were dissolved in 100 ml of methanol in a stainless steel air-tight, pressure-tight reactor of 250 ml volume. The reactor was rinsed out with hydrogen and then charged with hydrogen up to a pressure of 1 MPa. The mixture was heated to 50° C. and 5 times 0.1 g of 10% palladium on activated carbon were added portionwise, while stirring within 4 hours. The mixture was stirred for 2 hours further and then filtered. The filtrate was evaporated and the residue was distilled under reduced pressure to give 1.4 g (69.1% yield) of S-ethyl N,N-diethylthiolcarbamate boiling at 35°-38° C./8 Hgmm.

The following results were obtained by using the same procedure with other catalysts.

| Catalyst | Yield, % |
| --- | --- |
| Raney nickel | 72 |
| 10% platinum on activated carbon | 58.3 |
| Platinum black | 78.6 |
| RuCl$_2$(Ph$_2$P)$_3$ | 22.1 |
| IrBr(OO)(Ph$_3$P)$_3$ | 35.2 |

EXAMPLE 7

Catalytic transfer hydrogenation 2 g (10.6 mmoles) of S-vinyl N,N-di(n-propyl)-thiolcarbamate were dissolved in 100 ml of methanol in the reactor described in Example 6. After rinsing with hydrogen, the pressure of hydrogen was adjusted to 10 MPa. The mixture was heated to 50° C. and 5 times 0.1 g of Raney nickel were added within 4 hours. After finishing the addition, the mixture was stirred for additional 2 hours, the catalyst was filtered out, the filtrate was evaporated and the oily residue was distilled under reduced pressure to give 1.72 g (85.1% yield) of S-ethyl, N,N-di(n-propyl)-thiolcarbamate boiling at 80°-82° C./8 Hgmm.

EXAMPLE 8

Direct hydrogenation 20 ml of S-vinyl N,N-di(n-propyl)-thiolcarbamate were dissolved in 100 ml of methanol in a pressure vessel of 300 ml volume. After adding 1 g of 1% palladium on activated carbon, the vessel was closed, rinsed out three times with hydrogen, then charged with hydrogen up to a pressure of 1.5 MPa. The mixture was hydrogenated at 240° C. for 8 hours to give S-ethyl N,N-di(n-propyl)-thiolcarbamate in 82% yield, while 12% of the starting vinyl compound were recovered.

The compounds listed in the Table below were similarly prepared.

| Substances of the general formula (I) ($R^3 = R^4 = R^5 = R^6 = H$) | | | | | |
|---|---|---|---|---|---|
| $R^1$ | $R^2$ | Catalyst | Time hours | Temp. °C. | Yield % |
| n-Propyl | n-propyl | Raney-Ni | 4 | 200 | 100 |
| Ethyl | cyclohexyl | Pd on —Al$_2$O$_3$ | 4 | 240 | 100 |
| Ethyl | n-butil | Pd on —Al$_2$O$_3$ | 4 | 240 | 100 |
| —(CH$_2$)$_6$— | | Pd on —Al$_2$O$_3$ | 4 | 240 | 100 |

EXAMPLE 9

Process (b)

148 ml (1.2 moles) of diallylamine and 57.6 (1.8 atoms) of sulphur were charged into a reactor of 1000 ml volume. The reactor was filled with carbon monoxide up to a pressure of 5.9 MPa. After reacting at 100° C. for one hour, the reactor was pressurized with acetylene and the vinylation was carried out at 120° C. for additional 8 hours while acetylene was added several times. S-vinyl N,N-diallylthiolcarbamate was obtained in 10% yield.

EXAMPLE 10

Process (c)

25 ml (0.18 mole) of dipropylamine and 31.25 g (0.52 mole) of carbonyl sulphide were dissolved in 50 ml of methanol in a reactor of 300 ml working volume. The pressure of acetylene was adjusted to 1.7 MPa, then the reactor was heated to and kept at 130°–140° C. for 10 hours. After cooling down and blowing off the gas, the crude reaction mixture was distilled under reduced pressure to give 24.3 g (71% yield as calculated for dipropylamine) of S-vinyl dipropylthilcarbamate.

EXAMPLE 11

Additional alkylation 56 g (1.75 atoms) of sulphur and 154 ml (1.2 moles) of di(n-propyl)-amine were charged into a reactor of 1000 ml volume. After rinsing out the reactor with acetylene, the pressure of acetylene was adjusted to 1.7 MPa, that of carbon monoxide was regulated to 5.9 MPa. The mixture was first heated at 100° C. for 75 minutes, then at 120° C. for 14 hours, while acetylene was added several times.

The reaction mixture was transferred in a three-necked flask of 1000 ml volume, 400 ml of dioxane were added and 17.8 ml (0.22 mole) of ethyl iodide were dropped in under stirring. After removing the precipitate by filtration, the volatiles of the filtrate were evaporated and the residue was distilled under reduced pressure. A main fraction of 148 g boiling at 80°–98° C./1 mbar was obtained which contained 20% of S-ethyl di(n-propyl)-thiolcarbamate and 80% of S-vinyl di(n-propyl)-thiolcarbamate, i.e. a yield of 66% was calculated for di(n-propyl)-amine with a conversion of 71%.

What we claim is:

1. A process for the preparation of a thiolcarbamate ester of the formula (I)

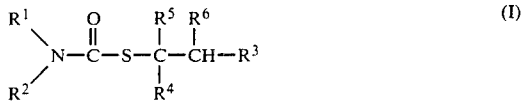

wherein
$R^1$ and $R^2$ stand independently for hydrogen or a straight or branched chain alkyl group containing 1 to 6 carbon atoms or an alkenyl group containing 2 to 6 carbon atoms, or an alkyl group containing 1 to 6 or alkenyl group containing 2 to 6 carbon atoms and mono- or polysubstituted by halogen, oxygen, sulphur and/or nitrogen; or
$R^1$ and $R^2$ together can represent an optionally substituted β,ω-alkylene group containing 4 to 6 carbon atoms;
$R^3$ and $R^4$ stand independently for hydrogen or an alkyl group containing 1 to 4 carbon atoms and optionally substituted by halogen or by a group containing oxygen, sulphur and/or nitrogen; and
$R^5$ and $R^6$ both stand for hydrogen; or
$R^5$ and $R^6$ together can represent a chemical bond, which comprises reacting
(a) thiolcarbamate salts of the formula (II)

wherein,
Y stands for a primary, secondary or tertiary ammonium ion or an alkaline metal ion; or
(b) amines of the formula (III)

together with sulphur and carbon monoxide; or
(c) amines of the formula (III) together with carbonyl sulphide and with an alkyne of the formula (IV)

and, hydrogenating the obtained product of formula (I), wherein of $R^5$ together with $R^6$ forms a chemical bond, to a compound of the formula (I), wherein both $R^5$ and $R^6$ stand for hydrogen.

2. A process as claimed in claim 1, process (a), which comprises using a solution of higher than 30% concentration of the thiolcarbamate salt.

3. A process as claimed in claim 1, process (a), which comprises carrying out the reaction in a melt of the thiolcarbamate salt.

4. A process as claimed in claim 1, process (a), which comprises carrying out the reaction at temperature between 80° and 200° C.

5. A process as claimed in claim 1, process (b), or process (c), which comprises carrying out the reaction at temperatures between 25° and 200° C.

6. A process as claimed in claim 1, process (a) or process (b), which comprises using an excess of sulphur or carbonyl sulphide, respectively, as related to the amount of the amine.

7. A process as claimed in claim 1, which comprises accomplishing the optionally desired hydrogenation by a catalytic transfer process.

8. A process as claimed in claim 1, which comprises accomplishing the optionally desired hydrogenation by a direct catalytic process.

9. A process as claimed in claim 7, which comprises using an excess of the hydrogen substance of the transfer hydrogenation as solvent.

10. A process as claimed in claim 8, which comprises hydrogenating under a hydrogen pressure of 0.1 to 10 MPa.

11. A process as claimed in claim 1, which comprises using N,N-di(n-propyl)-thiolcarbamate salts and acetylene, or di(n-propyl)-amine, sulphur, carbon monoxide and acetylene as starting materials.

12. A process as claimed in claim 1, which comprises using N,N-diethylthiolcarbamate salts and acetylene, or diethylamine, sulphur, carbon monoxide and acetylene as starting materials.

13. A process as claimed in claim 1, which comprises using N-ethyl-N-cyclohexylamine, sulphur, carbon monoxide and acetylene as starting materials.

14. A process as claimed in claim 1, which comprises using di(secondary-butyl)-amine, sulphur, carbon monoxide and acetylene as starting materials.

15. A process as claimed in claim 1, which comprises using N-ethyl-N-(n-butyl)-amine, sulphur, carbon monoxide and acetylene as starting materials.

16. A process as claimed in claim 1, which comprises using perhydroazepine, sulphur, carbon monoxide and acetylene as starting materials.

17. A process as claimed in claim 1, which comprises using 3-dimethylaminopropylamine, sulphur, carbon monoxide and acetylene as starting materials.

18. A process as claimed in claim 1, which comprises di(n-propyl)-amine, sulphur, carbon monoxide and 1-propyne as starting materials.

* * * * *